(12) United States Patent
Kariguddaiah

(10) Patent No.: US 12,085,984 B2
(45) Date of Patent: Sep. 10, 2024

(54) SMART WEARABLES AND NON-WEARABLE DEVICES WITH EMBEDDED NFC (NEAR FIELD COMMUNICATION), VITAL HEALTH SENSORS, ULTRA VIOLET GERMICIDAL IRRADIATION (UVGI) AND ARTIFICIAL INTELLIGENCE/MOBILE/CLOUD BASED VIRTUAL ASSISTANT PLATFORM/TECHNOLOGIES

(71) Applicant: Abijith Kariguddaiah, Contra Costa County, CA (US)

(72) Inventor: Abijith Kariguddaiah, Contra Costa County, CA (US)

(*) Notice: Subject to any disclaimer, the term of this patent is extended or adjusted under 35 U.S.C. 154(b) by 206 days.

(21) Appl. No.: 17/474,090

(22) Filed: Sep. 14, 2021

(65) Prior Publication Data

US 2021/0405689 A1    Dec. 30, 2021

Related U.S. Application Data

(63) Continuation-in-part of application No. 16/904,996, filed on Jun. 18, 2020, now Pat. No. 11,635,785.

(51) Int. Cl.
*G06F 3/0488* (2022.01)
*A61L 2/00* (2006.01)
(Continued)

(52) U.S. Cl.
CPC ............ *G06F 1/163* (2013.01); *A61L 2/0047* (2013.01); *A61L 2/24* (2013.01); *G06F 1/1652* (2013.01);
(Continued)

(58) Field of Classification Search
CPC ...... G06F 1/163; G06F 1/1652; G06F 3/0488; G16H 10/20; G16H 40/67; H04W 4/80;
(Continued)

(56) References Cited

U.S. PATENT DOCUMENTS 8,566,115 B2   10/2013   Moore
8,764,651 B2   7/2014    Tran
(Continued)

FOREIGN PATENT DOCUMENTS

WO    WO-1998016895 A1    4/1998

*Primary Examiner* — Lisa S Landis

(57) ABSTRACT

A system with plurality of smart wearable and non-wearable having embedded NFC (Near Field Communication) tags, vital health sensors and UV-C germicidal irradiation sources; a computer mobile/cloud implemented platform with an artificial intelligence or machine learning powered virtual assistant; and a central cloud server is provided for prevention of spread of pathogens and for monitoring and/ prediction of infection and timely intervention assistance for better health outcomes to the user, taking into account the underlying conditions of the user. The system includes a plurality of body wearables including, but not limited to, a hand glove, a footwear, a vest, a full body suit, a face mask, a footwear cover or a smart portables and at least one non-wearable portable smart device, and all of them with re-programmable NFC tags and UVGI source embedded within them, to dis-infect any surface the user desire, and to avoid touching any surfaces, and the same—each device of which having a plethora of various body health and viral monitoring sensors, embedded within them to transmit and upload data to mobile/cloud platform, to predict probability of infection and take necessary actions to provide better personalized health outcomes.

12 Claims, 16 Drawing Sheets

(51) Int. Cl.
   *A61L 2/24* (2006.01)
   *G06F 1/16* (2006.01)
   *G06N 20/00* (2019.01)
   *G16H 10/20* (2018.01)
   *G16H 40/67* (2018.01)
   *H04W 4/80* (2018.01)

(52) U.S. Cl.
   CPC ............ *G06F 3/0488* (2013.01); *G06N 20/00* (2019.01); *G16H 10/20* (2018.01); *G16H 40/67* (2018.01); *H04W 4/80* (2018.02); *A61L 2202/14* (2013.01); *A61L 2202/16* (2013.01)

(58) Field of Classification Search
   CPC ......... G06N 20/00; A61L 2/24; A61L 2/0047; A61L 2202/14; A61L 2202/16
   See application file for complete search history.

(56) References Cited

U.S. PATENT DOCUMENTS

| | | |
|---|---|---|
| 2002/0068857 A1 | 6/2002 | Iliff |
| 2006/0184393 A1 | 8/2006 | Ewin et al. |
| 2014/0276552 A1* | 9/2014 | Nguyen, Jr. ........ A61M 5/1723 705/2 |
| 2017/0000916 A1* | 1/2017 | Stibich ..................... A61L 9/18 |
| 2017/0216617 A1* | 8/2017 | Kariguddaiah ....... A61F 5/0118 |

* cited by examiner

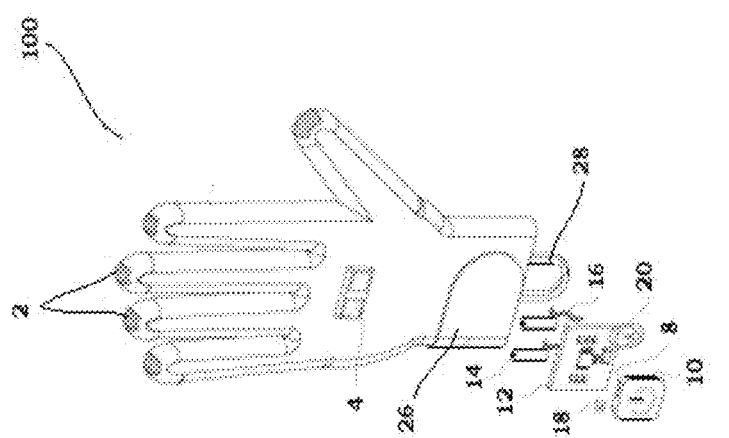

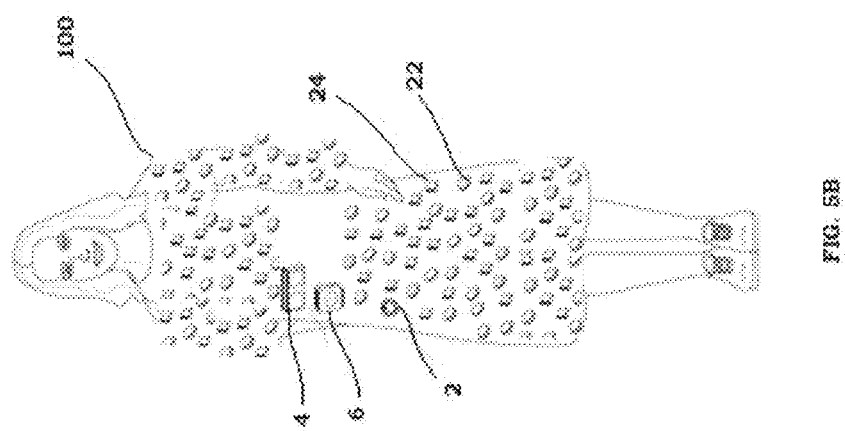

SMART WEARABLES AND NON-WEARABLE DEVICES WITH EMBEDDED NFC (NEAR FIELD COMMUNICATION), VITAL HEALTH SENSORS, ULTRA VIOLET GERMICIDAL IRRADIATION (UVGI) AND ARTIFICIAL INTELLIGENCE/MOBILE/CLOUD BASED VIRTUAL ASSISTANT PLATFORM/TECHNOLOGIES

CROSS-REFERENCE TO RELATED APPLICATIONS

This application claims the benefit of U.S. Non-provisional application Ser. No. 16/904,996 filed Jun. 18, 2020, by the present inventor; the disclosure is hereby incorporated herein by reference.

FIELD OF THE INVENTION

The present invention relates to a system of smart wearable/non-wearable devices and an AI/ML powered mobile smart platform with "smart virtual assistant" for preventive lifesaving health outcomes against pandemic and Health/Hospital Acquired infections. More particularly, it is a complete system comprising hardware devices such as smart wearables having an NFC embedded technologies for 'No-Touch' operations, a plethora of vital health monitoring sensors to monitor viral infection symptoms, an Ultraviolet Germicidal Irradiation (UVGI) source that disinfects the surface area where the wearer comes in contact with after wearing the smart wearable, or when inserted into the smart non-wearable and an AI powered mobile/cloud/computer implemented smart platform having a smart virtual assistant that accesses the real time health monitoring sensor data, and other available data specific to user, processes said data and accordingly manipulate working of the personalized health system for better outcomes.

BACKGROUND OF THE INVENTION

While Health Acquired Infections have been prevalent for a long time, now the world is facing outbreak of Covid-19, one of the biggest pandemic of a century, a contagious disease that is being spreads from person to person either by direct touch of infected person, through air when the infected person sneezes or coughs or by touching or using something an infected person has touched or used. One can protect him/herself up to some extent by washing hands well often, following social distancing norms and staying away from those who are sick.

But, not all these options are there for front line warriors, such as doctors, healthcare workers, their patients, average citizens, elderly, Military and Public servants' etc. as they all are always at constant risk of infection from their daily activities, not just only from the pandemics but also from a myriad of health/hospital acquired infections, which CDC (Center for Disease Control) has identified as a legitimate threat and has provided guidelines to combat them. In addition of being at constant risk of getting infected, the healthcare workers and doctors, for example, are also a significant factor in disease transmission from patient to patient by virtue of inadequate attention to, or inadequate technology for, sanitization. As the healthcare professionals go from patient to patient, they can transport pathogens present over their body, or simple wearables such as glove or vest or any other wearable. One touch of a hand or any part of a body having pathogens alive on it may contaminate all the surfaces coming in contact with it. For example, when the health care workers and physicians open doors, handle equipment while wearing gloves, they could be contaminating the doors if the pathogen exists on the glove, or picking up the pathogen from the door handle. Also, from a consumer's daily-life perspective, much of the same threats/reasons explained above applies, where the consumer have the potential to get infected while they go about dealing with high contact daily-life situations including travel in the car or in the airplane or any type of public transport, or in the home or office dealing with take-out/grocery delivery, purchases, etc., or of course in the health setting for all involved—patients, care givers and loved ones.

Normally, the healthcare personnel uses wearable such as gloves and PPE to protect themselves from getting infected by the pathogens, however these wearable cannot be washed easily while being worn, also they are not replaced as often as should be to limit the transmission of disease and also constant replacement of the wearable increases cost associated with the patient care. Thus, one of the effective method to disinfect the germs before it reaches the human body is by causing the germs' inability to replicate and exposure of pathogens to ultraviolet radiation has proven to be effective in causing the germs' inability to replicate, and this has been researched and proven by the professors at New York based Columbia university, specifically on Covid-19.

Therefore, during this emergency situation of covid-19 pandemic, and future pandemics and other health/hospital acquired infections, there exists a dire need of a complete smart system made of a smart wearables/non-wearable devices and an AI powered platform with smart virtual assistant for frontline healthcare workers and patients and others that may limit the need of touching the various surface by the wearer and also monitor the probability of infection in the body of the wearer, providing for early alert interventions and better outcomes, especially in the nursing or home-care settings. Also significantly, a need of an Artificial Intelligence powered smart virtual assistant is further there which may work in combination with smart wearable which having a plethora of health monitoring sensors to monitor the body condition of the wearer in real time to calculate probability of viral infection using AI—Artificial Intelligence and Machine Learning techniques, so that predictive analysis/preventive personalized care may be taken, providing better health outcomes and another layer of spread prevention. Also, there exists a need of a system having an AI powered smart platform which is compatible with other healthcare and/or interactive platform, both public and private, such as EMR (Electronic Medical Records), Google, Amazon, Apple, etc. Health Platforms, that may work as an interface to connect the wearer with the platform of system/devices.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The present invention provides a system made of a smart wearables and non-wearable devices, having embedded NFC (Near Field Communication) technology, plethora of health monitoring sensors and a UV-C Germicidal technology and a mobile/cloud/computer implemented AI powered smart platform with a smart virtual assistant. The smart wearables of present invention intends to save lives and provide preventative health outcomes using a plurality of health monitoring sensors that measures a critical data of the wearer such as temperature, blood pressure, Oxygen level, etc. and uploads it on the server while the smart virtual assistant of the AI powered platform, using said data and the artificial intelligence of the platform, calculates the probability of severe viral infection such as Covid-19 and informs it to the wearer as well as other medical personal so that the preventive care may be taken before it is too late.

According to one embodiment, the plethora of health monitoring sensors monitors the body health condition of the wearer in real time whereas the NFC technology present within the smart wearable/non-wearable of present system makes the 'no-touch' condition possible as the wearer just needs to point the NFC tags present within the smart wearables towards the NFC readers to facilitate many touch less activities such as opening doors or getting access without touching, answering calls or making payments, etc. in a present like emergency situations which could become the new-normal, where social distancing and avoiding touching to any unnecessary surface is a key requirement.

Further, each smart wearable and non-wearable further includes an embedded UV-C germicidal irradiation (UVGI) technology which is provided to make the wearer capable of disinfecting the surface area that comes into contact with the smart wearables. The smart wearables & portables of present invention is embedded with a UV-C light source ranging from 200 nm to 350 nm for various appliable wearable use case scenarios that disinfects any bacteria and/or pathogens coming in contact with the wearable thus protecting the wearer from any infection. Further, it disinfects any area the wearer touches hence protecting others touching the same area and stopping the spread of the infection thus making much safer environment. According to one embodiment, the smart wearable and non-wearable further includes a proximity and a pressure sensor as a safety sensors configured to turn ON the smart wearables only when the user grabs something with certain amount of pressure and/or only when within close proximity (less than 1-2 cms) of the touch area, thereby protecting the wearer from any UV-C exposure.

According to one embodiment, the UVGI technology of present invention has proven to be effective against many hospitals acquired infections, SARS and MERS, a similar virus strains to Covid-19, and hence it is effective against Covid-19 too. The UV-C radiation of the UVGI technology modifies the RNA/DNA and eliminates the ability of the pathogens to reproduce and the pathogens that can't reproduce are not infectious, and are therefore harmless. The UVGI of the present smart wearables are capable of deactivating pathogens such as, but not limited to, Influenza, the common flu, anthrax, smallpox, viral hemorrhagic fever, pneumonic plague, tularemia, drug resistant tuberculosis and Covid-19.

According to one embodiment, the smart wearable and non-wearable further includes a multipurpose portable sanitation device which can be used in many settings (in the car, or in the air, in the office, in the nurses pockets or purses, or at home) where the user may disinfect anything (stuff) that fits into the openings provided, such that the stuff is free of viruses after disinfection and can be safely used, thereby protecting the wearer or loved ones from any viral exposure.

According to one embodiment, the smart wearables is any of the gloves, shoes, vest, full body suit, face mask, footwear cover or any smart portable devices having all the above mentioned features embedded within the wearables which ensures that the area which is being touched by any smart wearable worn by the wearer may receive 100% UVGI radiation such that maximum area get disinfected ensuring maximum EFFICIENCY and EFFICACY of the UVGI mechanism, providing best case safety scenarios for user environment.

According to one embodiment, the smart wearables are any of the gloves, shoes, vest, full body suit, face mask, footwear cover or any smart non-wearables and portables having all or any of the above mentioned features embedded within them, therefore providing the ability to the wearer to disinfect anything hence not only offers germicidal safety to user, but also an important means of preventing the spread of infection and germs, and over constant usage over time, makes the user environment more and more safer. Further, the system includes flexible non-wearable devices that are comprising of plethora of sensors and UV-C sources which is provided to allow user to use the sensors to measure real time body condition as well as the UV-C sources allows user to disinfect any other product or object from any pathogen present over the surface of said object.

According to one embodiment, the plethora of health monitoring sensors of the smart wearable and non-wearable tracks reading with accuracy including temperature, blood oxygenation level, blood pressure, heart rate, etc. and uploads that real time readings over the cloud server. According to one embodiment, the AI powered virtual assistant of present system uses said real time data being uploaded over the server, and using the Artificial Intelligence of the system, determines the probability of getting infections. According to one embodiment, the AI/machine learning based mobile/cloud/computer implemented platform of present invention which in conjunction with a 'smart virtual assistant" interrogates the real time sensory data from the cloud server and using pre-defined algorithms derived by physician recommendations, creates a questions for the wearer regarding his/her personal health condition, and if required, triggers the execution of a Q&A session with other expert healthcare personals. According to one embodiment, the smart virtual assistant further provides answers of the initially created questions back to the physician or expert healthcare personal, to provide for just in time care, and early diagnosis for better and preventive outcomes. This makes possible, an early detections, warnings and hence aids in early interventions for the patient, while also preventing the spread of a disease.

Additionally, the smart wearables and non-wearables of present invention includes an EKG sensor, a pulse detection sensor and other health monitoring sensors. Over time, an establishment may now have enough data on the user/wearer such that new technologies including Machine Learning/Artificial Intelligence may produce better outcomes to both the user, their insurers, and establishments.

The inner layers of the smart wearables, according to one embodiment, that makes contact with the skin is made of a Celliant synthetic fabric material which is known to trap the body's infrared energy and cycle it back to improve oxygenation within the body as well as resolve minor aches and pain.

In healthcare facilities, the smart wearables facilitates the healthcare workers and physicians to use NFC technology to open doors, answer calls etc. without touching anything and just by waving their hand or by pointing a tag present within any of the smart wearable such as gloves or shoes or vest to a specific NFC reader for any practical purpose. While, at the same time, the wearer can disinfect any surface, such as the door handle or any other product or equipment by touching or making a contact of the smart wearable with the surface which needs to be disinfected.

According to one embodiment, the present invention provides a system having plurality of smart wearables embedded with the plethora of various sensors to monitor and send the vital data to the cloud server in real time. The smart wearables is any of the wearable including, but not limited to, gloves, shoes, vest, full body suit, face mask, footwear cover or any other smart and portable non-wearable having all the above mentioned features embedded within them. The smart wearables and the portable non-wearables of present system comprises a UV light source or diodes that emits UV rays to disinfect the surfaces which comes in contact with said smart wearables.

According to one embodiment, The system further includes a computer implemented platform with a 'smart virtual assistant (SVA)' coupled with the mobile application or cloud server which is powered by the Artificial Intelligence or a Machine learning Algorithm that monitors the vital body data of the patient user in real time and based on physician set triggers specific to the patient and/or user, automatically interrogates the patient as a first line of nurse or physician derived questions and answers, accordingly notifies the responsible nurse or healthcare personnel and a family members of the wearer about the real time probability of viral infection or other disease conditions, providing for a preventive approach to patient care. Further, the AI/Mobile/Cloud/computer implemented platform of present invention behaves as a smart nursing assistant to the user which analyzes present and past medical history of the user/patient and based on the triggers specific to the patient set by the dedicated healthcare personal of the wearer, the platform automatically prepares a set of questions for the wearer, gets the required approvals by the personal physician taking into account any underlying conditions of the said patient, etc., similar to the ones which the nurse or physician generally asks when consulted for the first time during a typical physician or nursing engagement. The wearer using the mobile application, may answer that question directly using voice/text in the phone or by using any other smart device with embedded system and integrated platform such as the Amazon Alexa, Apple Siri, and Google Assistant etc. that records the answers of the wearer and directly stores it over the cloud to allow the personal physician or a family members to check or monitor by accessing the mobile/cloud/computer implemented platform of present system, thereby vastly improving time based critical health outcomes.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

FIG. 1B shows same back view of a smart glove with an exploded view of an electronic control unit.

FIG. 5B exemplarily illustrate an embodiment of a smart half vest as a smart wearable of present invention.

DETAILED DESCRIPTION OF INVENTION

Figure 1A:
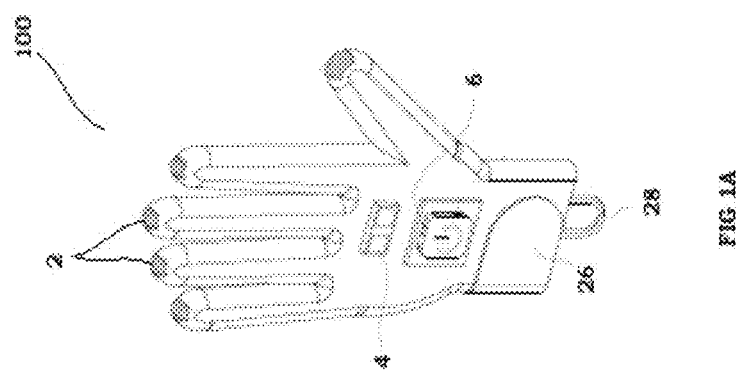
FIG. 1A shows a back view of a smart hand glove as a smart wearable of present invention.

The embodiment herein and the various features and advantageous details thereof are explained more fully with reference to the non-limiting embodiments and detailed in the following description. Descriptions of well-known components and processing techniques are omitted so as to not unnecessarily obscure the embodiments herein. The examples used herein are intended merely to facilitate an understanding of ways in which the method and embodiments herein may be practiced and to further enable those of skill in the art to practice the embodiments herein. Accordingly, the examples should not be construed as limiting the scope of the embodiments herein.

The disclosure of present invention provides a smart wearables and non-wearables for better health outcomes by preventing spread of infection from day-to-day activities, to facilitate early detection and prevention of potential infections, to work as a smart Personal Protective Equipment for the frontline healthcare and defense workers and their patients, to work as a digital key to open doors, operate smartphones, card exchange, disinfect any personal gadgets or devices etc. without touching anything, and to disinfect any surface, product or equipment using the smart wearables and non-wearable portable devices. According to one embodiment, the smart wearables of present invention includes all the body wearable such as, but not limited to, a hand gloves, a foot wear, a body wear i.e. a vest, a full body suit or any other portable means and also includes a non-wearable flexible smart devices. All the smart devices and wearables of present invention are embedded with: a plethora of health vital sensors to monitor real time body health condition of the wearer; a re-programmable NFC (near field communication) tags that allows wearer to do many things without having to touch any surface; an Ultraviolet Germicidal Irradiation (UVGI) light sources to disinfect any surface that wearer touches or desire to disinfect; and a celliant fabric as an inner layer where the skin comes in contact with the wearables, where the celliant fabric traps the body's infrared energy and cycles it back within the body to improve oxygenation and resolves minor aches and pains.

According to one embodiment, the smart wearables and non-wearables of present invention might also work as an additional complementary smart PPE layer of protection for front line health care workers who are at constant risk from infections. The plethora of health or vital sign monitoring sensors of the smart wearables continuously monitors and reports the real time body health condition to hospital system and to the healthcare professionals, therefore provides better safety by early detection and prevention of the spread of the pathogens such as covid-19 which can be deciphered based on increase in body temperature and drop in blood oxygen levels.

According to one embodiment, the smart wearables of present invention is comprising of a sensors such as, but not limited to, a temperature sensor, a blood oxygenation sensor, a blood pressure or pulse detection sensor, an EKG and other popular sensors as the industry proliferates. The smart wearables and non-wearables of the present invention further includes an electronic control units having a communication module that collects the data from all these sensors, compares it with pre-defined limits and sends the warning or alert signal over the mobile applications to the person of concern to prevent the spread of an infection. Further, the electronic control unit of the smart wearables and non-wearables stores the data over the cloud to create a historic data set for the caregivers to deliver better outcomes.

According to one embodiment, the smart wearables and non-wearables of present invention further includes a safety sensors such as a proximity sensor and a pressure sensor that are configured to turn on the smart wearables and non-wearables only when the wearer grabs or touches something with certain amount of pressure, thereby protecting the wearer from any UV light exposure issues.

The re-programmable NFC chips and tags embedded within the smart wearables are configured to allow user to do many touch activities without having to touch any surface that might be contaminated by the infection like answering phones, opening or closing doors, sending social media messages, payment mechanism, etc. Further, the NFC tags are re-programmable and hence can be programmed to do specific functions in conjunction with the localized NFC readers.

According to one embodiment, the ultraviolet germicidal irradiation (UVGI) light sources of different strength are provided within the smart wearables and non-wearables of present invention to disinfect the area coming in contact with the surface of the smart wearables. The UV-C radiation of the UVGI sources modifies the RNA/DNA and eliminates the ability of a pathogen to reproduce. The pathogen that can't reproduce are not infectious, and are therefore harmless. The effectiveness of UVGI derives from a band of UV-C radiation centered at a wavelength of 265 nm plus or minus 60 nm.

Furthermore, the smart wearables are any of the gloves, shoes, vest, full body suit, face mask, footwear cover or any smart portables and non-wearables having all the above mentioned features embedded within the wearables, including the Smart Glove, ensures that all the surface area of the touch area required to do any particular activity such as a hold, handshake, clasp, grab, etc., receives 100% UVGI radiation such that 100% of the users touches, are disinfected ensuring maximum EFFICIENCY and EFFICACY of the UVGI mechanism, providing best case safety scenarios for user environment.

The smart non-wearable portable devices are provided also with plethora of health monitoring sensors and plurality of UV-C light emitters which is provided to allow any user to easily carry the device without wearing on a body. The portable devices are not wearable over the body of the user as a smart PPE, however it is flexible and portable which allows any user to easily carry it in the purse or in a nurses pocket, as examples. The sensors configured within the body and/or walls of the device allows the user to bring the hand, wrist or any part of the body near the sensor to monitor the health of the user. Moreover, because of the flexible joints within the non-wearable device, it is capable of changing embodiment to form a structure such as container or a shed under which any object or other devices can be placed to dis-infect using the UV-C light emitting sensors present within the flexible smart device.

Now, referring to FIG. 1A that shows a back view of a smart hand glove 100 as a smart wearable of present invention. According to present embodiment, the smart glove 100 is comprising of an NFC tags 2 embedded within all the fingertips of the smart glove 100. A sensory unit 4 having a plurality of various sensors such as a blood temperature sensor, a blood oxygenation sensor, a proximity and pressure sensors, and a motion sensor to respectively monitor the blood temperature, oxygen level, distance and pressure over the glove 100 and a movement of a wrist or ankle. According to one embodiment, an electronic control unit 6 is also configured within the smart glove 100 that works as a brain of the smart gloves that manages power distribution to all the other electronic components, collects data from the sensors, identifies the risk or emergency situation from the sensory data and accordingly sends alert signals to the mobile application of the person of concern as well as stores the data over the cloud for future reference. This cloud data may be accessed by the user, the establishment, and/or the doctors for better outcomes. According to one exemplary embodiment, the smart glove 100 of present invention may further comprise a strap 26 to close the glove 100 securely over the hand and a strap 28 to pull glove onto hand.

FIG. 1B shows back view of a same smart glove 100 with an exploded view of an electronic control unit 6. According to present embodiment, the electronic control unit is further comprising of; a touch screen 8 with a power switch 10 on screen 8 that is configured to allow wearer to manually start or stop working of the smart glove 100 or to manipulate operation of the smart glove 100 using the touch screen 8; a printed circuit board 12 having a micro controller and a communication module, where the micro controller allows for the power management of the different type of light sources user within the smart wearables, drives the touch screen for various functions including powering the device, collects the data from all the sensors, uploads that data over a cloud for future reference, determines the emergency condition and sends the alert signal over the mobile application of a person of concern.

The electronic control unit 6 of present invention is further comprising of a rechargeable batteries 14 to provide power for functioning of all the electronic components of the smart wearable 100. A wire 16 that connects the electronic components with the electronic control unit 6. According to one embodiment, a temperature sensor 18 and a blood pressure or pulse detection sensor 20 is configured within the electronic control unit to respectively monitor body temperature and a pulse rate of the wearer.

Figure 2:
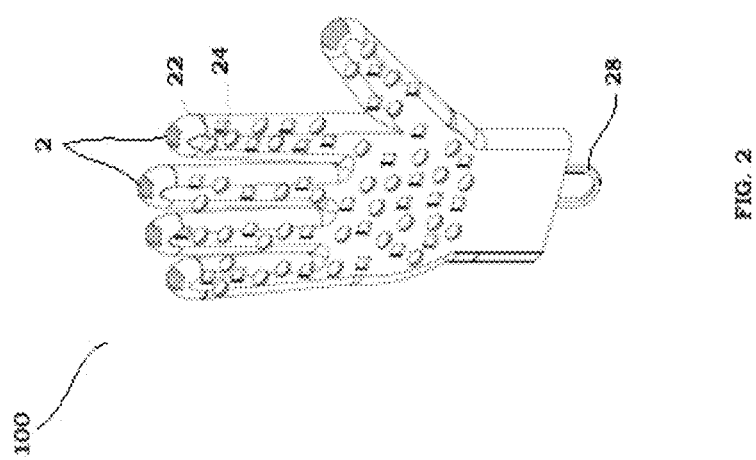
FIG. 2 shows a front view of the smart glove disclosed in FIGS. 1A and 1B of present invention.

FIG. 2 shows a front view of the smart glove 100 disclosed in FIGS. 1A and 1B of present invention. The smart glove 100 includes plurality of UV-C light sources 22 and 24 of respective intensity of 265 nm and 310 nm mounted within the palm area of the glove such that all the surface area touched by the person may receive UV irradiation to disinfect whole area.

Figure 3:
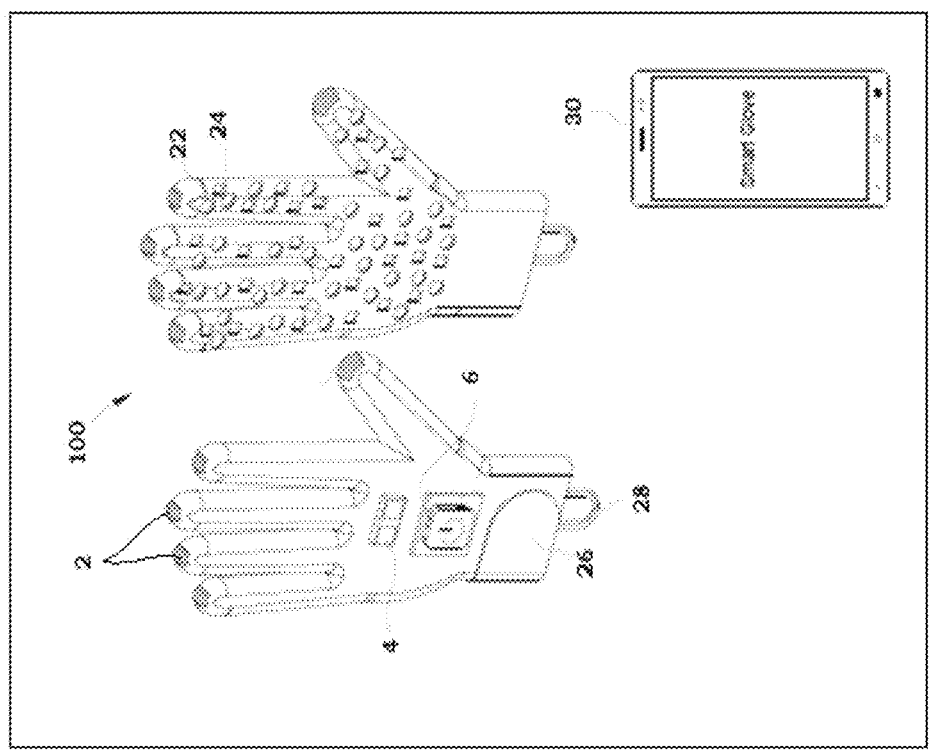
FIG. 3 shows complete system of smart wearable having both the gloves and a smart user device having mobile application.

FIG. 3 illustrates an exemplary embodiment of pair of a smart gloves 100 as a smart wearable of present invention along with monitoring using the mobile application 112 installed within the smart device 30. According to one embodiment, the electronic control unit 6 allows connectivity of the smart wearables with the mobile application 30. The mobile application 112 allows user and caregivers to monitor the real time health data from the sensors as well as allows re-programming of the NFC tags to do specific functions in conjunction with the localized NFC readers. The mobile application further allows user to access the cloud in future to get a historic data set.

Figure 4:
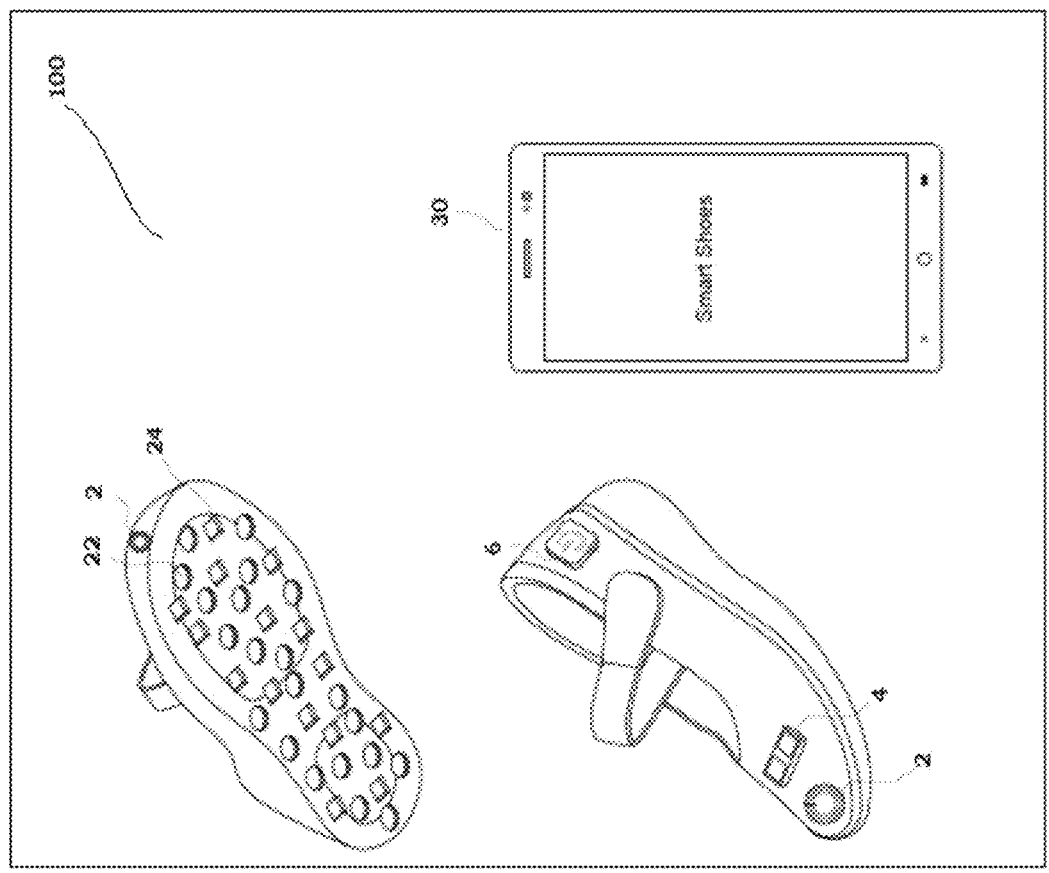
FIG. 4 illustrates an exemplary embodiment of a smart shoes as a smart wearable of present invention along with monitoring using the mobile application.

FIG. 4 illustrates an exemplary embodiment of a smart shoes 100 as a smart wearable of present invention along with monitoring using the mobile application 112. For the sake of easy understanding, all the smart wearables shown in figures are numbered with the same number 100. According to present invention, the smart shoes also comprises all the components that were present in the smart glove. The smart shoe 100 also comprises an NFC tags 2 mounted at front point of the shoe 100; a sensory unit 4 having plurality of various sensors on the top portion; an electronic control unit 6 on the sides of the shoe 100 and a plurality UV-C light sources 22 and 24 mounted within the sole at the bottom of the smart shoes 100.

Figure 5A:
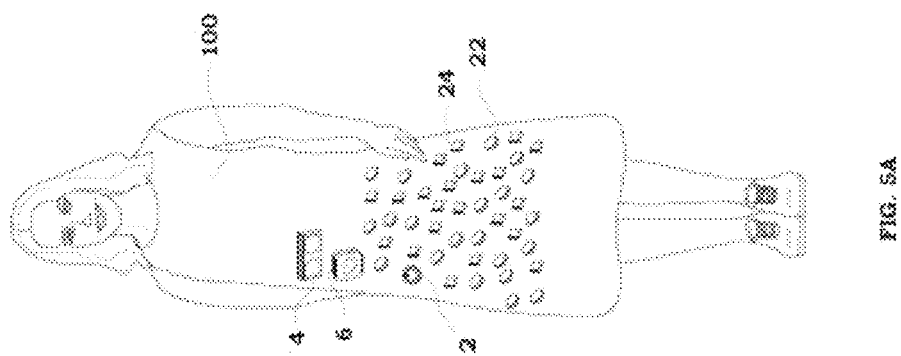
FIG. 5A exemplarily illustrate an embodiment of a smart full vest as a smart wearable of present invention.
Figure 6:
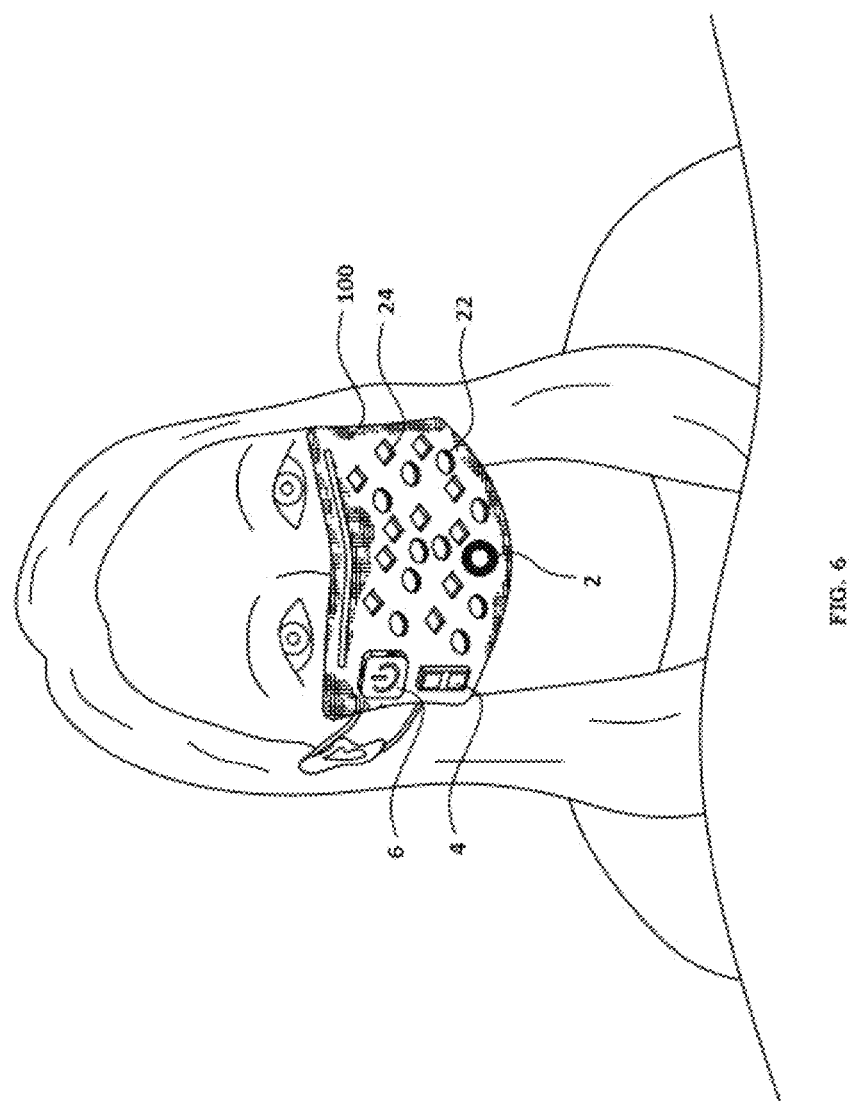
FIG. 6 exemplarily illustrates an embodiment of a face mask as a smart wearable of present invention.

FIG. 5A and FIG. 5B exemplarily illustrate an embodiment of a smart half vest 100 and smart full vest 100 respectively as a smart wearable of present invention that are also comprising of all the components of the smart wearables mounted at different location within the smart vest 100. While, FIG. 6 illustrates and embodiment of a smart face mask 100 as a smart wearable of present invention comprising all the novel component and functional features same as other smart wearables of present invention.

Figure 7B:
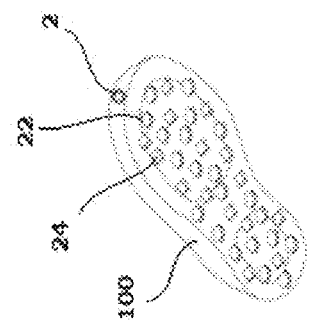
FIG. 7A and FIG. 7B exemplarily illustrates an embodiment of a shoe cover worn over the shoes for temporary purposes as a smart wearable of present invention.
Figure 7A:
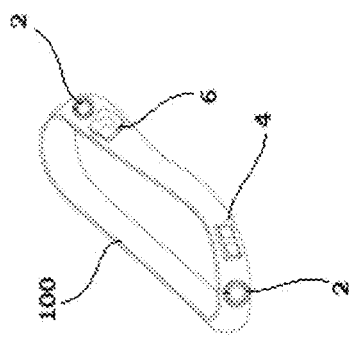

FIG. 7A and FIG. 7B exemplarily illustrates an embodiment of a shoe cover 100 as a smart wearable of present invention. According to this embodiment, it allows user to wear this smart cover on any shoes instead of wearing a specific smart shoes. The shoes cover also includes all the components such as an NFC tags 2, a sensory unit 4, an electronic control unit 6, a UVGI light sources and all the other components same as other smart wearable of present invention.

Figure 8:
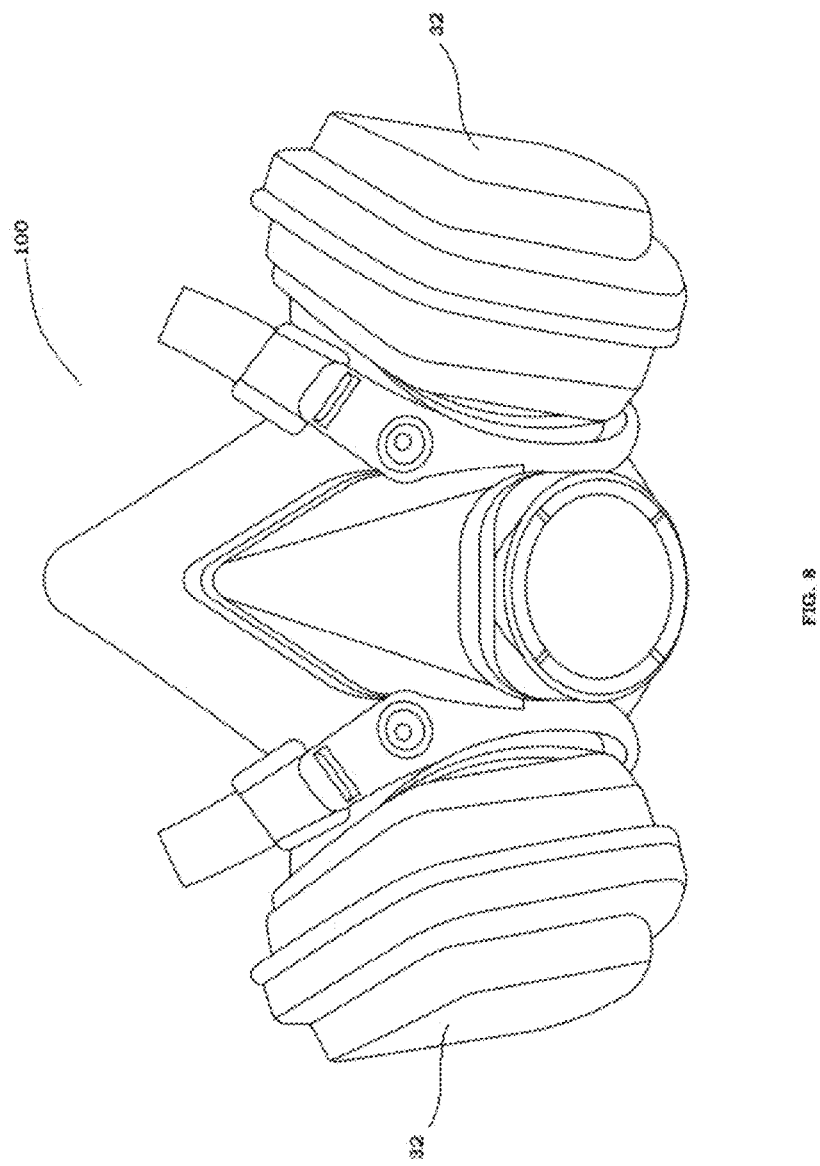
FIG. 8 illustrates one another exemplary embodiment of the face mask wherein the UVGI source is contained within the external protected air—inlet protrusions.

While, FIG. 8 illustrates one another exemplary embodiment of the face mask 100 wherein the UV source is contained within the external protrusions 32 instead of direct embedding within the body of the smart wearables. According to one embodiment, the face mask 100 is comprising of all the other components same as other smart wearables and includes a pair of separate external protrusions 32 having a UVGI light sources where the external protrusions 32 encloses the UVGI light sources to prevent unnecessary exposure of the UV radiation. According to one embodiment, all the smart wearbales of present invention are ergonomic, thin, waterproof, and washable for reuse.

Figure 9:
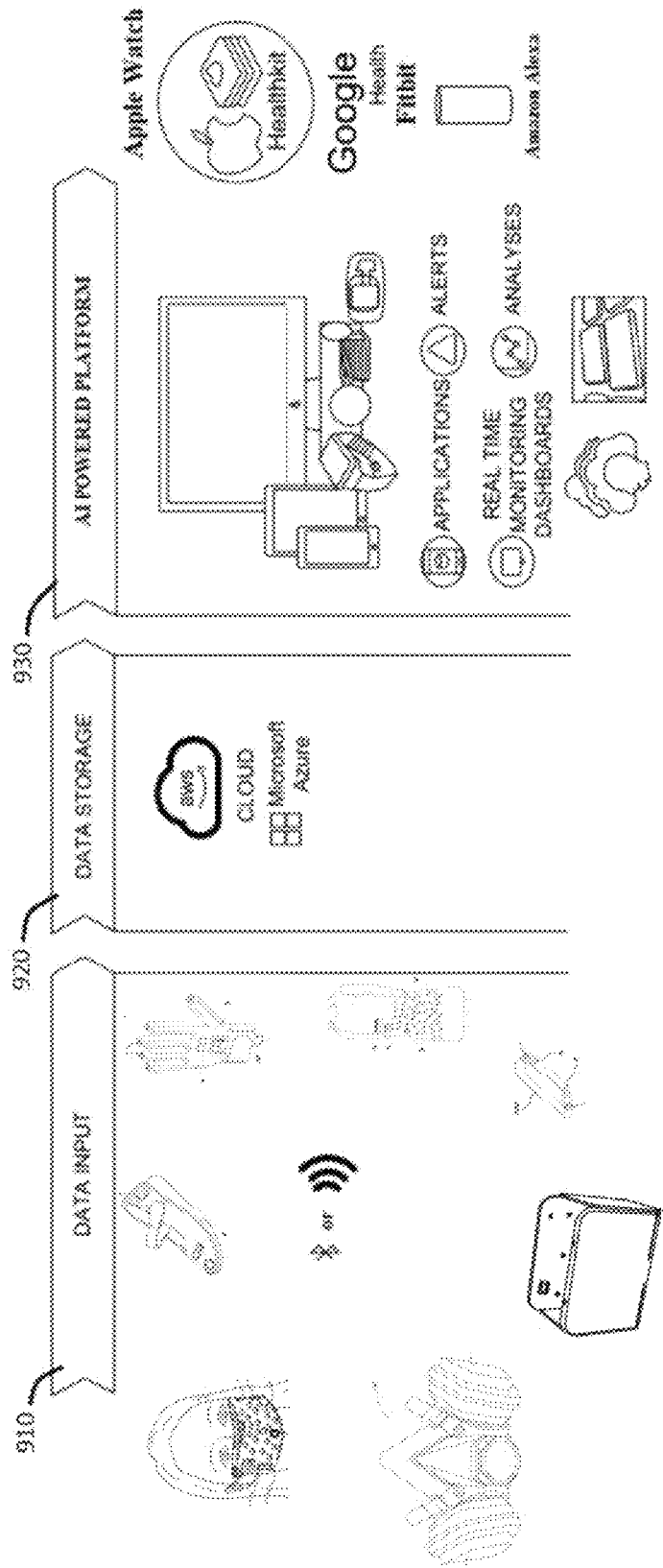
FIG. 9 shows a data flow diagram of present LLLT wrap system having a different wrap devices and the computer implemented AI/ML powered platform with smart virtual assistant (SVA).

Referring to FIG. 9 now which shows a data flow diagram of viral infection monitoring and prevention system wherein the system is made of plurality of smart wearable devices as a data input units 910 that are capable of monitoring as well as disinfecting the parts of the body where it is being worn to save the wearer from the virus using the UVGI technology. All the smart wearable devices of the system includes a plurality of Ultraviolet Germicidal Irradiation (UVGI) source that emit the UV-C light of uniform wavelength and intensity at the respective part of the body of user as well as on all the surfaces which comes in contact with the part of the body of wearer where the smart wearable is worn. According to one embodiment, the UVGI source of each smart wearable is further manipulated by the AI M1—PSA powered computer implemented platform depending on the real time condition of the wearer.

The smart wearables of the system works as a data input unit which includes plurality of different vital health data sensors to monitor the vital body data of the user in real time. Each smart wearable of present invention further includes an electronic circuit or unit having a processor and a communication module to transmit the data from sensors to the cloud server of the system which works as a data storage unit 920 of present system. According to one embodiment, the data storage unit or a cloud server 920 is a centralized server to store the data from the data inputs 910 in real time. The centralized cloud server of present invention is any third party cloud server.

According to one embodiment, the present mobile/cloud server 920 is capable of being accessed by the AI powered mobile/cloud/computer implemented platform with PSA 930 for data acquisition, data interrogation and manipulation. The computer implemented platform acquires said real time sensory data from the cloud server 920, processes said data using machine learning algorithms and artificial intelligence of present computer implemented platform 930 and provides real time dashboard of said data over the platform for the wearer and the person of concern of the wearer.

According to one embodiment, the AI/Mobile/Cloud/computer implemented platform, based on analysis of real time vital sensor data and the users personal health data, especially related to any underlying conditions, using the AI and machine learning algorithms, alerts the wearer as well as medical/healthcare persons of concern and family members, in case any situation arises such as increase of any vital body data from a threshold normal limit, such as steady drop in blood oxygen levels or when high probability of viral infection is detected in the body of the wearer which is determined by the AI powered SVA assistant using the real time sensory data. This threshold data limit is set by the system for doctor approval and/or by the doctor or personal physician for the said wearer. According to one embodiment, when such high probability is detected or when wearer himself wants to consult his medical personnel, he may raise the request over the platform by accessing it through smart user device of the wearer. Based on the request by the wearer or when detected high probability, the AI powered platform of present invention automatically notifies the medical personal while the Smart Virtual Assistant (SVA) of the wearer present within the system and activates the patients specific pre-determined questionnaire for the patient to answer at the convenience of his home, and convenience of devices/etc.

The answers are automatically collected and notified to the personalized physician/nurse, thereby providing for a mechanism for the 1$^{st}$ interactions. i.e. questions of answers that typically a nurse asks before the physician gets involved, to be conducted painlessly and at the patients convenience at home or anywhere they are. This early screening, provides for a positive timely intervention that has the potential to prevent deadly consequences. The physician/nurse, with this set of answers and corollary data, can determine the next course of actions for the said patient, and surely provide for better TIMELY for better preventive health outcomes. Each patient's specific questions based on the existing conditions that the wearer currently has and the questions are also approved by the wearer's doctor such that its relevant personalized medicine, may be provided for better TIMELY 'personalized' outcomes or timely emergency preventive steps may be taken to prevent the wearer from suffering from deadly viral infection complications. The AI/mobile/cloud/computer implemented platform with smart virtual assistant of present invention alerts the wearer and all the concern persons by vibrating the smart device of the user or via sound, text or message notification over the smart device of the user. The computer implemented platform 930 of present invention is further capable of being interfaced with the third party healthcare devices or platforms such as Amazon Alexa, Google fitbit, and Apple Health—watch EMR (Electronic Medical Record) systems etc.

According to one embodiment, the AI/Mobile/Cloud/computer implemented platform 930 with PSA of present invention further behaves as a smart assistant for the wearer or user, where the platform 930 analyzes vital sensory data of the user continuously, and based on pre-determined set of conditions, launches a screen interactive questionnaire for the user in which the user is asked to answer specific questions that generally a personal physician would ask when interviewing the wearer for the first time. The AI and the machine learning algorithms, based on the analyzed vital body data as well as past medical history of the user, prepares a questionnaire for the wearer.

This questionnaire is originally available in the mobile/cloud server and the AI and/or ML powered platform of present invention chooses the standard care questions that makes sense for the specific patient, which is also personalized to the said patients existing conditions, and make it available for the patient and his physician to approve and to use. According to one embodiment, the prepared questions by the AI/ML powered smart virtual assistant of the platform are further edited and finalized and confirmed by the personal physician such that it's uniquely tailored to the specific patient with the triggers set by the physician to enable these Q&A again specific to the wearer (For example—if the patient is diabetic and know for high blood pressure—the doctor sets the trigger as 3 continuous days of 90/160 where the system triggers the Q&A and get the answers quickly to the physician so point of care with immediate intervention can lead to better patient outcomes.

According to one embodiment, the smart wearable platform of present invention is also capable to execute voice enabled Q&A session via system integrated third party platforms of choice of user, such as, via Apple Siri on the phone, or via Amazon Alexa or using Google home assistant. The computer implemented platform 930 with PSA of present invention allows user to answer said question by many different ways using the smart user device in which the present computer implemented platform is installed or by using any other synced third party healthcare device with the platform 930 interfaced. The system allows user to submit the answers of the questions raised by the platform 930 via text or voice on the smart phone with the platform installed or through any other interfaced third party devices such as Amazon Alexa, Apple Siri, Google Assistant etc.

Figure 10:
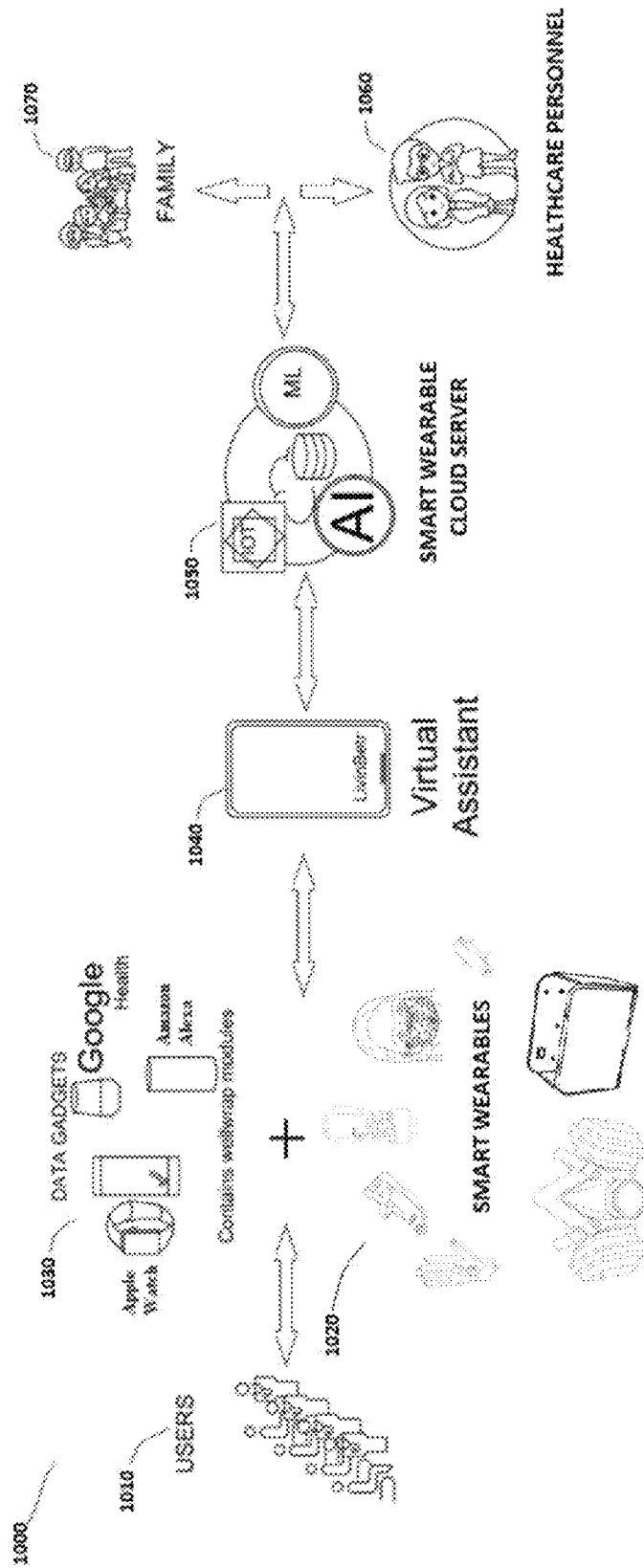
FIG. 10 shows a block diagram of present system with an integrated virtual assistant within the platform.

FIG. 10 shows a flow diagram of present system 1000 with an integrated virtual assistant within the platform. According to present embodiment, the system 1000 includes an AI and/or ML backed virtual assistant that depending on the preset triggers by the personal physician of the wearer, creates a customized 'personalized' questions based on the real time vital sensory data of the patient, which the physician may normally ask the wearer before consultation. According to present embodiment, the virtual assistant 1040 of present computer implemented platform is continuously in contact with the wearable smart devices 1020 and the third party healthcare devices 1030 of the user 1010 integrated with the present system 1000.

Further, according to present embodiment, the virtual assistant 1040 of the system 1000 further stores said data and questionnaire over the cloud server 1050 for the personal physician 1060 and the family members or loved ones 1070 to access it through their personal smart devices. According to one embodiment, the wearable smart devices is any smart device of present system 1000 worn on any part of the body of the wearer 1010. According to one embodiment, the third party data gadgets 1030 integrated with present system 1000 is any of the healthcare or smart device such as smart wearable devices (smart watches, bands etc.) or any other healthcare device such as Amazon Alexa, Google Health, etc.

According to one embodiment, apart from the wearable devices, the present system further includes a flexible and compact smart non-wearable device also having a plurality sensors present within them to monitor the body condition of the user, however these devices requires user to manually bring any body part new the sensor configured within the device so that the device may monitor respective sensory data.

Figure 11A:
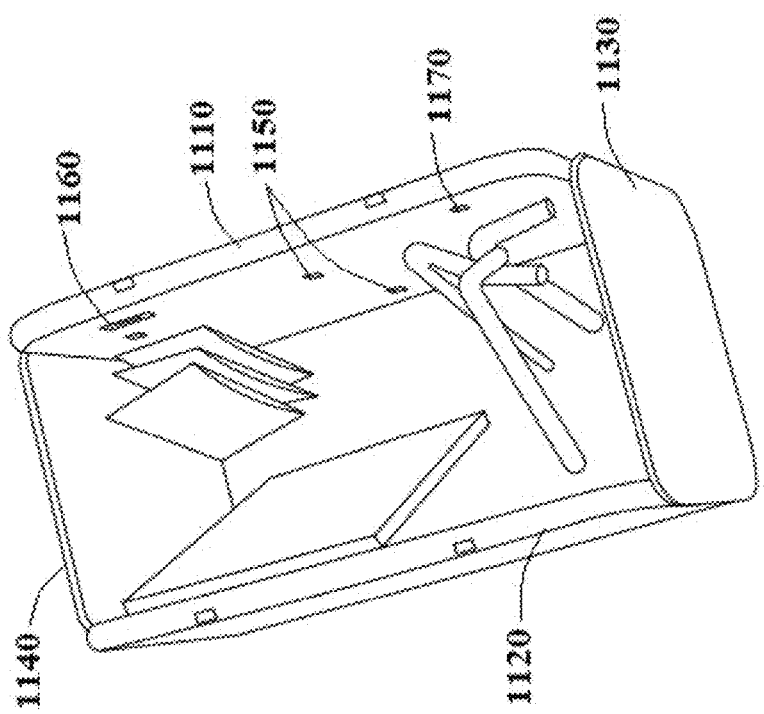
FIG. 11A shows view of one exemplary embodiment of a flexible smart non-wearable device in the form of container.
Figure 11B:
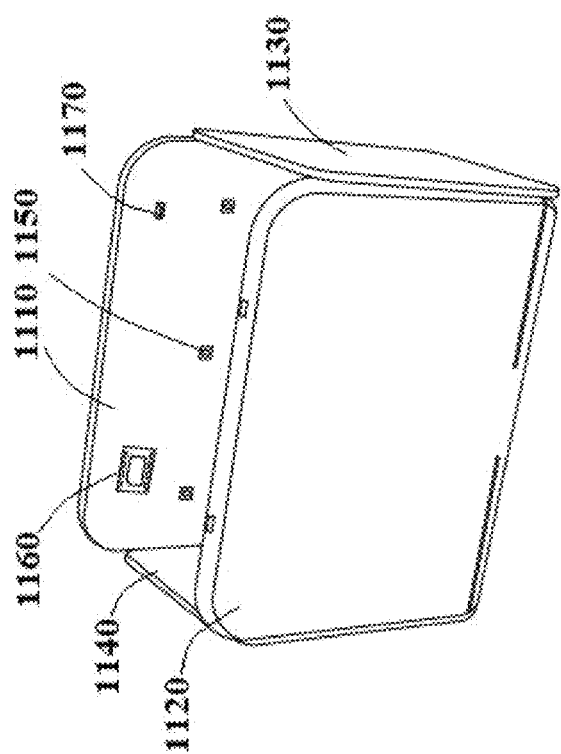
FIG. 11B shows isometric view of the flexible smart non-wearable device of FIG. 11A.

FIG. 11A and FIG. 11B shows one exemplary portable smart non-wearable device 1100, wherein the device is made of plurality of walls or sheets connected with each other through a flexible joints allowing user to form various shapes such as container or shed from the device to dis-infect any other small objects such as books, mobile phones, vehicle keys, food packages and many more other objects. According to present embodiment, the walls of the portable smart device 1100 is turned to form a container shape in which other products or objects may be places to dis-infect the surfaces of said products or objects.

According to present embodiment, the portable smart non-wearable device 1100 is made of a front wall 1110, a base, a back wall 1120 connected in the same order using a flexible connection mechanism which allows the angle between them to be changed to form shapes. Further, at least one side wall (1130 & 1140) flexibly attached at each side. According to one embodiment, the side walls (1130 & 1140) are removably coupled using a fastening members. According to present embodiment, all the walls are configured at right angle with the base creating a container shape having a cavity where any other object of smaller size may get placed.

According to one embodiment, the inner surface of both the front wall 1110 and back wall 1120 includes plurality of UV-C light sensors 1150 configured to emit ultra-violet lights of various strengths and frequency over the products or an object placed within the device 1100 to dis-infect the surface of said product. According to one embodiment, the device 1100 further includes plurality of various sensors configured within the walls of the device 1100. According to present embodiment, a temperature monitoring sensor 1160 is configured at the inner surface of the front wall 1110 which is configured to allow user to check the real time body temperature of the user by bringing any body part of the user near the temperature sensor 1160.

According to one embodiment, the device 1100 further includes a control unit having a communication unit to send the data monitored by the sensor over the server of the system which the user may access and check using a smartphone or any other smart device of the user. Moreover, the flexible smart device 1100 includes other sensors such as blood oxygen monitoring sensor 1170, pulse monitoring sensor etc. to allow user to check his vital body data.

Figure 12:
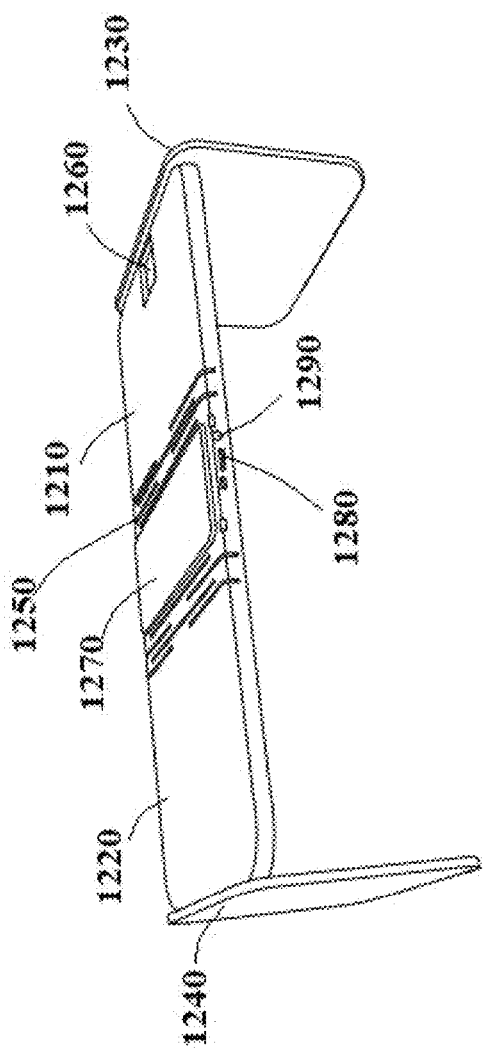
FIG. 12 shows open embodiment of the flexible smart non-wearable device shown in FIG. 11A.

FIG. 12 shows one another embodiment of flexible portable smart non-wearable of FIG. 11 formed a shape of shed by changing placement of walls. According to present embodiment, the front wall, the base and the back wall of FIG. 11 is made as a single sheet by aligning the front sheet 1210 and back sheet 1220 with the base 1270, where the flexible joints or connections 1250 allows change in position of each wall with respect to others. According to present embodiment, the side walls of embodiment explained in FIG. 11 works as a pillar in present embodiment to hold the single sheet formed with the front sheet 1210, base 1270 and the back sheet 1220 forming a shed beneath it where any object and/product such as books can be placed to dis-infect it using the UV-C light.

According to present embodiment, the UV-C light sources present at the inner wall will emit the ultra-violet light over the product placed beneath the sheet to dis-infect. According to one embodiment, the device further includes a battery module present within the base 1270 along with the control unit for functioning of all the electronic components of the device. According to one embodiment, a display unit is configured at the outer surface of the front wall 1210 which displays the vital sensory data when the user checks using the sensors configured within the device.

According to present embodiment, the non-wearable flexible device further include a charging port 1280 which is configured to allow user to charge their smart phone or any other small smart user device. According to one embodiment, the non-wearable device further includes a manual press button 1290 to ON or OFF the non-wearable device.

Figure 13:
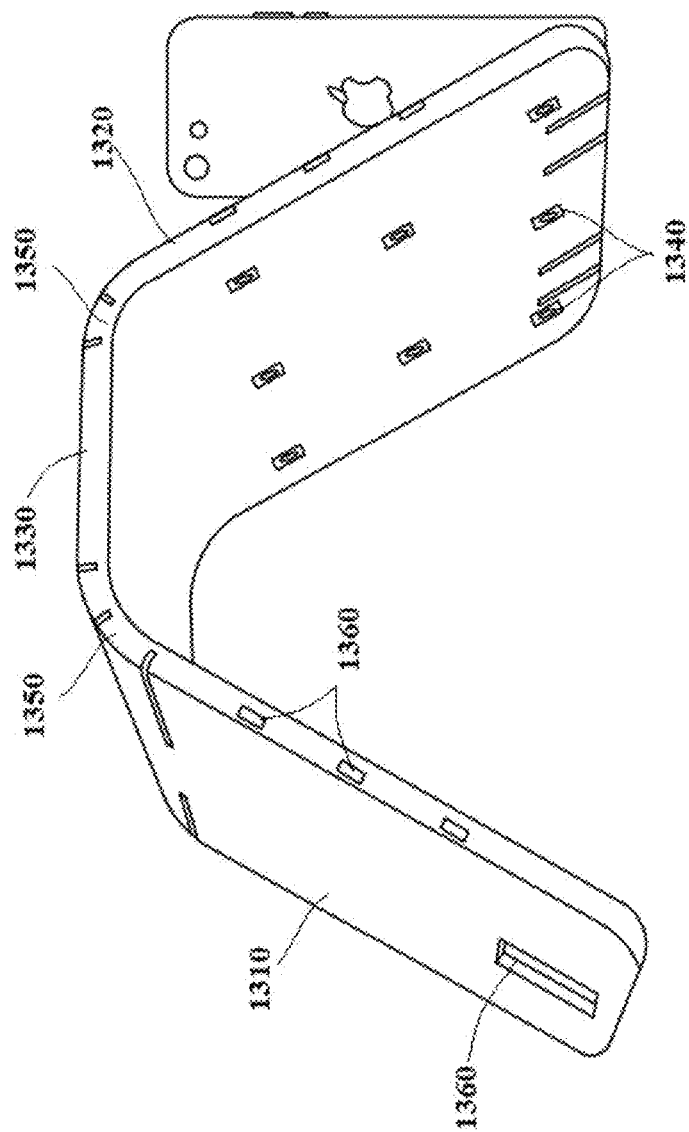
FIG. 13 shows view of the flexible smart non-wearable device without side walls in the shape of inverse V.

Now, FIG. 13 discloses one more embodiment of present flexible smart non-wearable device without detachable side walls. According to present embodiment, the device only includes a front wall 1310, rear wall 1320 and a base 1330 similar to all other embodiments of the non-wearable device, where the device includes an attachment members 1360 on the sides of the front wall 1310 and rear wall 1320 to detachably attach the side walls when required. The flexible connection mechanism 1350 between the base 1330 and both the walls allows the walls to tilt with respect to base to form various shapes or to form a cavity within which other smaller products may be placed to disinfect using the UV-C light source 1340 of the device.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A multifunctional smart system for preventing pathogen spread and/or providing better health outcomes, comprising;
   - a plurality of different smart wearables for different parts of a body of a user;
   - at least one smart non-wearable flexible device;
   - a computer implemented platform with an Artificial intelligence or Machine learning powered virtual assistant and a central mobile or cloud platform server;
   - wherein each of the plurality of different smart wearable and at least one smart non-wearable flexible device comprising;
     - an Ultraviolet Germicidal Irradiation (UVGI) light source configured over the smart wearables and the non-wearable flexible device;
     - a celliant fabric as an inner layer of the wearable;
     - a plurality of re-programmable NFC (near field communication) tags mounted within a body of plurality of different smart wearables and at least one smart non-wearable flexible device;
     - a plurality of different health monitoring sensors embedded to monitor real time body health condition of a wearer; and
     - a safety sensors comprising of a proximity and a pressure sensor which are configured to turn ON the UVGI light sources only when the wearer grabs or touches something with certain amount of pressure or close proximity.

2. The multifunctional smart system of claim 1, wherein the celliant fabric traps the body's infrared energy and cycles it back within the body to improve oxygenation and resolves minor aches and pains.

3. The multifunctional smart system of claim 1, is further comprising of a NFC tags that allows user to do many touch activities without having to touch any surface.

4. The multifunctional smart system of claim 1, wherein the health monitoring sensors measure a critical health data of the wearer.

5. The multifunctional smart system of claim 4, wherein the analyzed data is compared based on pre-determined set conditions and past medical history of the user.

6. The multifunctional smart system of claim 5, wherein the AI implemented platform calculates the probability of severe viral infection based on the data measured by the health sensors.

7. The multifunctional smart system of claim 6, wherein based on the analyzed data the platform launches a screen and text interactive questionnaire for the user.

8. The multifunctional smart system of claim 7, wherein the AI based Mobile or cloud computer implemented platform with an Artificial intelligence or Machine learning powered virtual assistant is capable to execute customized voice enabled pre-determined Q&A session with user via system integrated third party platform of choice of user.

9. The multifunctional smart system of claim 8, wherein the AI based Mobile or Cloud computer implemented platform with an Artificial intelligence or Machine learning powered virtual assistant interrogates the patient as a first line of nurse or physician derived questions and answers, and accordingly notifies the responsible nurse or healthcare personnel and a family members of the wearer about the real time probability of the health condition.

10. The multifunctional smart system of claim 1, wherein the AI based Mobile or cloud computer implemented platform with an Artificial intelligence or Machine learning powered virtual assistant interrogates real time data and executes Q&A session with other expert healthcare personnel for early detection and early interventions for the patient.

11. The multifunctional smart system of claim 1, wherein the AI based Mobile or Cloud computer implemented platform with an Artificial intelligence or Machine learning powered virtual assistant is configured to interface with the third party healthcare devices or platforms and Electronic Medical Record (EMR) systems to provide analysis and better health outcomes.

12. The multifunctional smart system of claim 1, wherein the AI based Mobile or Cloud computer implemented platform with an Artificial intelligence or Machine learning powered virtual assistant stores the voice and text Q&A data and analyzed data over the cloud for additional AI analysis, reporting and consumption by various expert healthcare personnel.

* * * * *